(12) United States Patent
Drees et al.

(10) Patent No.: US 8,757,485 B2
(45) Date of Patent: Jun. 24, 2014

(54) SYSTEM AND METHOD FOR USING CLINICIAN PROGRAMMER AND CLINICIAN PROGRAMMING DATA FOR INVENTORY AND MANUFACTURING PREDICTION AND CONTROL

(75) Inventors: Scott Drees, Dallas, TX (US); Norbert Kaula, Arvada, CO (US); Yohannes Iyassu, Denver, CO (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/604,285

(22) Filed: Sep. 5, 2012

(65) Prior Publication Data
US 2014/0061304 A1    Mar. 6, 2014

(51) Int. Cl.
*G06F 19/00* (2011.01)
*G06Q 10/08* (2012.01)

(52) U.S. Cl.
CPC .......... *G06Q 10/087* (2013.01); *G06F 19/3487* (2013.01)
USPC ............... 235/385; 607/30; 607/31; 235/494; 235/462.01

(58) Field of Classification Search
USPC ............... 235/375, 385, 494, 462.01, 472.01; 607/30, 31, 36
See application file for complete search history.

(56) References Cited

U.S. PATENT DOCUMENTS

| | | | |
|---|---|---|---|
| 4,432,360 A | 2/1984 | Mumford et al. | |
| 5,286,202 A | 2/1994 | De Gyarfas et al. | |
| 5,304,206 A | 4/1994 | Baker, Jr. et al. | |
| 5,312,446 A | 5/1994 | Holschbach et al. | |
| 5,370,672 A | 12/1994 | Fowler et al. | |
| 5,383,914 A | 1/1995 | O'Phelan | |
| 5,421,830 A | 6/1995 | Epstein et al. | |
| 5,628,776 A | 5/1997 | Paul et al. | |
| 5,713,937 A | 2/1998 | Nappholz et al. | |
| 5,722,999 A | 3/1998 | Snell | |

(Continued)

FOREIGN PATENT DOCUMENTS

| | | |
|---|---|---|
| EP | 1192972 | 4/2002 |
| EP | 2277586 | 1/2011 |

(Continued)

OTHER PUBLICATIONS

Synalink Features, SynaMed Web Page, http://synamed.com/synalinkFeatures.html., Copyright 2010, 2 pgs.

(Continued)

*Primary Examiner* — Christle I Marshall
(74) *Attorney, Agent, or Firm* — Haynes and Boone, LLP

(57) ABSTRACT

The present disclosure involves a medical system. The medical system includes a medical device configured to deliver a medical therapy to a patient, a clinician programmer configured to program the medical device, and a manufacturing database configured to store and maintain an electronic inventory of a plurality of types of medical devices. The clinician programmer is configured to acquire a visual representation of the medical device, generate an electronic ticket identifying the medical device based on the visual representation, and send the electronic ticket to the manufacturing database. The manufacturing database is configured to receive the electronic ticket from the clinician programmer and perform at least one of the following tasks in response to the received electronic ticket: updating the electronic inventory, analyzing a usage trend of the medical device, predicting a potential shortage of the medical device, and suggesting a production schedule for the medical device.

41 Claims, 10 Drawing Sheets

(56) References Cited

U.S. PATENT DOCUMENTS

| | | |
|---|---|---|
| 5,724,996 A | 3/1998 | Piunti |
| 5,819,740 A | 10/1998 | Muhlenberg |
| 5,879,374 A | 3/1999 | Powers et al. |
| 5,905,500 A | 5/1999 | Kamen et al. |
| 5,938,690 A | 8/1999 | Law et al. |
| 6,016,447 A | 1/2000 | Juran et al. |
| 6,016,448 A | 1/2000 | Busacker et al. |
| 6,052,624 A | 4/2000 | Mann |
| 6,083,156 A | 7/2000 | Lisiecki |
| 6,148,233 A | 11/2000 | Owen et al. |
| 6,154,675 A | 11/2000 | Juran et al. |
| 6,216,036 B1 | 4/2001 | Jenkins et al. |
| 6,246,414 B1 | 6/2001 | Kawasaki |
| 6,249,705 B1 | 6/2001 | Snell |
| 6,278,890 B1 | 8/2001 | Chassaing et al. |
| 6,307,554 B1 | 10/2001 | Arai et al. |
| 6,308,102 B1 | 10/2001 | Sieracki et al. |
| 6,345,200 B1 | 2/2002 | Mouchawar et al. |
| 6,386,882 B1 | 5/2002 | Linberg |
| 6,442,432 B2 | 8/2002 | Lee |
| 6,525,727 B1 | 2/2003 | Junkins et al. |
| 6,564,104 B2 | 5/2003 | Nelson et al. |
| 6,587,104 B1 | 7/2003 | Hoppe |
| 6,611,267 B2 | 8/2003 | Migdal et al. |
| 6,622,048 B1 | 9/2003 | Mann et al. |
| 6,669,631 B2 | 12/2003 | Norris et al. |
| 6,786,405 B2 | 9/2004 | Weidenhoefer |
| 6,852,080 B2 | 2/2005 | Bardy |
| 6,882,982 B2 | 4/2005 | McMenimen et al. |
| 6,895,280 B2 | 5/2005 | Meadows et al. |
| 6,920,360 B2 | 7/2005 | Lee et al. |
| 6,931,155 B1 | 8/2005 | Gioia |
| 6,961,448 B2 | 11/2005 | Nichols et al. |
| 6,961,617 B1 | 11/2005 | Snell |
| 7,003,349 B1 | 2/2006 | Andersson et al. |
| 7,034,823 B2 | 4/2006 | Dunnet |
| 7,058,453 B2 | 6/2006 | Nelson et al. |
| 7,060,030 B2 | 6/2006 | Von Arx et al. |
| 7,065,409 B2 | 6/2006 | Mazar |
| 7,066,910 B2 | 6/2006 | Bauhahn et al. |
| 7,076,303 B2 | 7/2006 | Linberg |
| 7,087,015 B1 | 8/2006 | Comrie et al. |
| 7,092,761 B1 | 8/2006 | Cappa et al. |
| 7,107,102 B2 | 9/2006 | Daignault et al. |
| 7,142,923 B2 | 11/2006 | North et al. |
| 7,181,286 B2 | 2/2007 | Sieracki et al. |
| 7,181,505 B2 | 2/2007 | Haller et al. |
| 7,184,837 B2 | 2/2007 | Goetz |
| 7,239,926 B2 | 7/2007 | Goetz |
| 7,266,412 B2 | 9/2007 | Stypulkowski |
| 7,299,085 B2 | 11/2007 | Bergelson et al. |
| 7,359,751 B1 | 4/2008 | Erickson et al. |
| 7,373,204 B2 | 5/2008 | Gelfand et al. |
| 7,440,806 B1 | 10/2008 | Whitehurst et al. |
| 7,452,336 B2 | 11/2008 | Thompson |
| 7,463,927 B1 | 12/2008 | Chaouat |
| 7,474,223 B2 | 1/2009 | Nycz et al. |
| 7,481,759 B2 | 1/2009 | Whitehurst et al. |
| 7,489,970 B2 | 2/2009 | Lee et al. |
| 7,496,403 B2 | 2/2009 | Cao et al. |
| 7,499,048 B2 | 3/2009 | Sieracki et al. |
| 7,505,815 B2 | 3/2009 | Lee et al. |
| 7,551,960 B2 | 6/2009 | Forsberg et al. |
| 7,602,384 B2 | 10/2009 | Rosenberg et al. |
| 7,617,002 B2 | 11/2009 | Goetz |
| 7,627,372 B2 | 12/2009 | Vaisnys et al. |
| 7,640,059 B2 | 12/2009 | Forsberg et al. |
| 7,657,317 B2 | 2/2010 | Thacker et al. |
| 7,685,005 B2 | 3/2010 | Riff et al. |
| 7,711,603 B2 | 5/2010 | Vanker et al. |
| 7,720,549 B2 | 5/2010 | Schroeppel et al. |
| 7,747,330 B2 | 6/2010 | Nolan et al. |
| 7,774,067 B2 | 8/2010 | Keacher et al. |
| 7,778,710 B2 | 8/2010 | Propato |
| 7,801,596 B2 | 9/2010 | Fischell et al. |
| 7,801,611 B2 | 9/2010 | Persen et al. |
| 7,805,199 B2 | 9/2010 | KenKnight et al. |
| 7,822,483 B2 | 10/2010 | Stone et al. |
| 7,853,323 B2 | 12/2010 | Goetz |
| 7,885,712 B2 | 2/2011 | Goetz et al. |
| 7,890,180 B2 | 2/2011 | Quiles et al. |
| 7,928,995 B2 | 4/2011 | Daignault |
| 7,934,508 B2 | 5/2011 | Behm |
| 7,940,933 B2 | 5/2011 | Corndorf |
| 7,953,492 B2 | 5/2011 | Corndorf |
| 7,953,612 B1 | 5/2011 | Palmese et al. |
| 7,957,808 B2 | 6/2011 | Dawant et al. |
| 7,978,062 B2 | 7/2011 | LaLonde et al. |
| 7,991,482 B2 | 8/2011 | Bradley |
| 8,014,863 B2 | 9/2011 | Zhang et al. |
| 8,021,298 B2 | 9/2011 | Baird et al. |
| 8,027,726 B2 | 9/2011 | Ternes |
| 8,046,241 B1 | 10/2011 | Dodson |
| 8,060,216 B2 | 11/2011 | Greenberg et al. |
| 8,068,915 B2 | 11/2011 | Lee et al. |
| 8,068,918 B2 | 11/2011 | Vallapureddy et al. |
| 8,078,440 B2 | 12/2011 | Otto et al. |
| 8,082,162 B2 | 12/2011 | Flood |
| 8,121,702 B2 | 2/2012 | King |
| 8,135,566 B2 | 3/2012 | Marshall et al. |
| 8,140,160 B2 | 3/2012 | Pless et al. |
| 8,140,167 B2 | 3/2012 | Donders et al. |
| 8,160,328 B2 | 4/2012 | Goetz et al. |
| 8,160,704 B2 | 4/2012 | Freeberg |
| 8,165,385 B2 | 4/2012 | Reeves et al. |
| 8,187,015 B2 | 5/2012 | Boyd et al. |
| 8,200,324 B2 | 6/2012 | Shen et al. |
| 8,200,340 B2 | 6/2012 | Skelton et al. |
| 8,219,206 B2 | 7/2012 | Skelton et al. |
| 8,233,991 B2 | 7/2012 | Woods et al. |
| 8,246,680 B2 | 8/2012 | Betz et al. |
| 8,249,713 B2 | 8/2012 | Fang et al. |
| 8,255,060 B2 | 8/2012 | Goetz et al. |
| 8,323,218 B2 | 12/2012 | Davis et al. |
| 8,326,433 B2 | 12/2012 | Blum et al. |
| 8,340,775 B1 | 12/2012 | Cullen et al. |
| 8,382,666 B1 | 2/2013 | Mao et al. |
| 8,386,032 B2 | 2/2013 | Bachinski et al. |
| 8,401,666 B2 | 3/2013 | Skelton et al. |
| 8,428,727 B2 | 4/2013 | Bolea et al. |
| 2001/0037220 A1 | 11/2001 | Merry et al. |
| 2003/0076301 A1 | 4/2003 | Tsuk et al. |
| 2003/0107572 A1 | 6/2003 | Smith et al. |
| 2003/0139652 A1 | 7/2003 | Kang et al. |
| 2003/0171911 A1 | 9/2003 | Fairweather |
| 2003/0177031 A1 | 9/2003 | Malek |
| 2004/0088374 A1 | 5/2004 | Webb et al. |
| 2004/0122477 A1 | 6/2004 | Whitehurst et al. |
| 2004/0210273 A1 | 10/2004 | Wang |
| 2005/0107831 A1 | 5/2005 | Hill et al. |
| 2005/0149356 A1 | 7/2005 | Cyr et al. |
| 2005/0168460 A1 | 8/2005 | Razdan et al. |
| 2005/0277872 A1 | 12/2005 | Colby et al. |
| 2006/0089888 A1 | 4/2006 | Roger |
| 2006/0100832 A1 | 5/2006 | Bowman |
| 2006/0241720 A1 | 10/2006 | Woods et al. |
| 2006/0242159 A1 | 10/2006 | Bishop et al. |
| 2006/0282168 A1 | 12/2006 | Sherman et al. |
| 2007/0078497 A1 | 4/2007 | Vandanacker |
| 2007/0093998 A1 | 4/2007 | El-Baroudi et al. |
| 2007/0179349 A1 | 8/2007 | Hoyme et al. |
| 2007/0203537 A1 | 8/2007 | Goetz et al. |
| 2007/0203538 A1 | 8/2007 | Stone et al. |
| 2007/0203543 A1 | 8/2007 | Stone et al. |
| 2007/0213790 A1 | 9/2007 | Nolan et al. |
| 2008/0004674 A1* | 1/2008 | King et al. ............. 607/46 |
| 2008/0004675 A1 | 1/2008 | King et al. |
| 2008/0033303 A1 | 2/2008 | Wariar et al. |
| 2008/0046036 A1 | 2/2008 | King et al. |
| 2008/0140161 A1 | 6/2008 | Goetz et al. |
| 2008/0149701 A1* | 6/2008 | Lane ..................... 235/375 |
| 2008/0177362 A1 | 7/2008 | Phillips et al. |
| 2008/0218517 A1 | 9/2008 | Holmdahl |
| 2008/0254944 A1* | 10/2008 | Muri et al. ............ 482/8 |

(56) References Cited

U.S. PATENT DOCUMENTS

| | | |
|---|---|---|
| 2008/0262565 A1 | 10/2008 | Bentwich |
| 2009/0018617 A1 | 1/2009 | Skelton et al. |
| 2009/0018619 A1 | 1/2009 | Skelton et al. |
| 2009/0024178 A1 | 1/2009 | Hennig |
| 2009/0048871 A1 | 2/2009 | Skomra |
| 2009/0089034 A1 | 4/2009 | Penney et al. |
| 2009/0099624 A1 | 4/2009 | Kokones et al. |
| 2009/0132009 A1 | 5/2009 | Torgenson et al. |
| 2009/0136094 A1 | 5/2009 | Driver et al. |
| 2009/0196471 A1 | 8/2009 | Goetz et al. |
| 2009/0234873 A1 | 9/2009 | Li et al. |
| 2009/0264967 A1 | 10/2009 | Giftakis et al. |
| 2009/0281596 A1 | 11/2009 | King et al. |
| 2010/0004033 A1 | 1/2010 | Choe et al. |
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0023343 A1 | 2/2011 | Turner et al. |
| 2011/0038498 A1 | 2/2011 | Edgar |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennet et al. |
| 2011/0093030 A1 | 4/2011 | Goetz et al. |
| 2011/0093047 A1 | 4/2011 | Davis et al. |
| 2011/0093051 A1 | 4/2011 | Davis et al. |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0224523 A1 | 9/2011 | Burdiman |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0192874 A1 | 8/2012 | Bolea et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0277828 A1 | 11/2012 | O'Conner et al. |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296392 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |
| 2013/0087609 A1* | 4/2013 | Nichol et al. ............... 235/375 |

FOREIGN PATENT DOCUMENTS

| | | |
|---|---|---|
| WO | WO 9959106 | 11/1999 |
| WO | WO 0209808 | 2/2002 |
| WO | WO 02084637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Boston Scientific Corporation, "Boston Scientific Precision Spectra System Programming Manual", Copyright 2010, 580 pgs.

Norbert Kaula et al., Office Action dated Nov. 21, 2013 for U.S. Appl. No. 13/600,684, 17 pages.

* cited by examiner

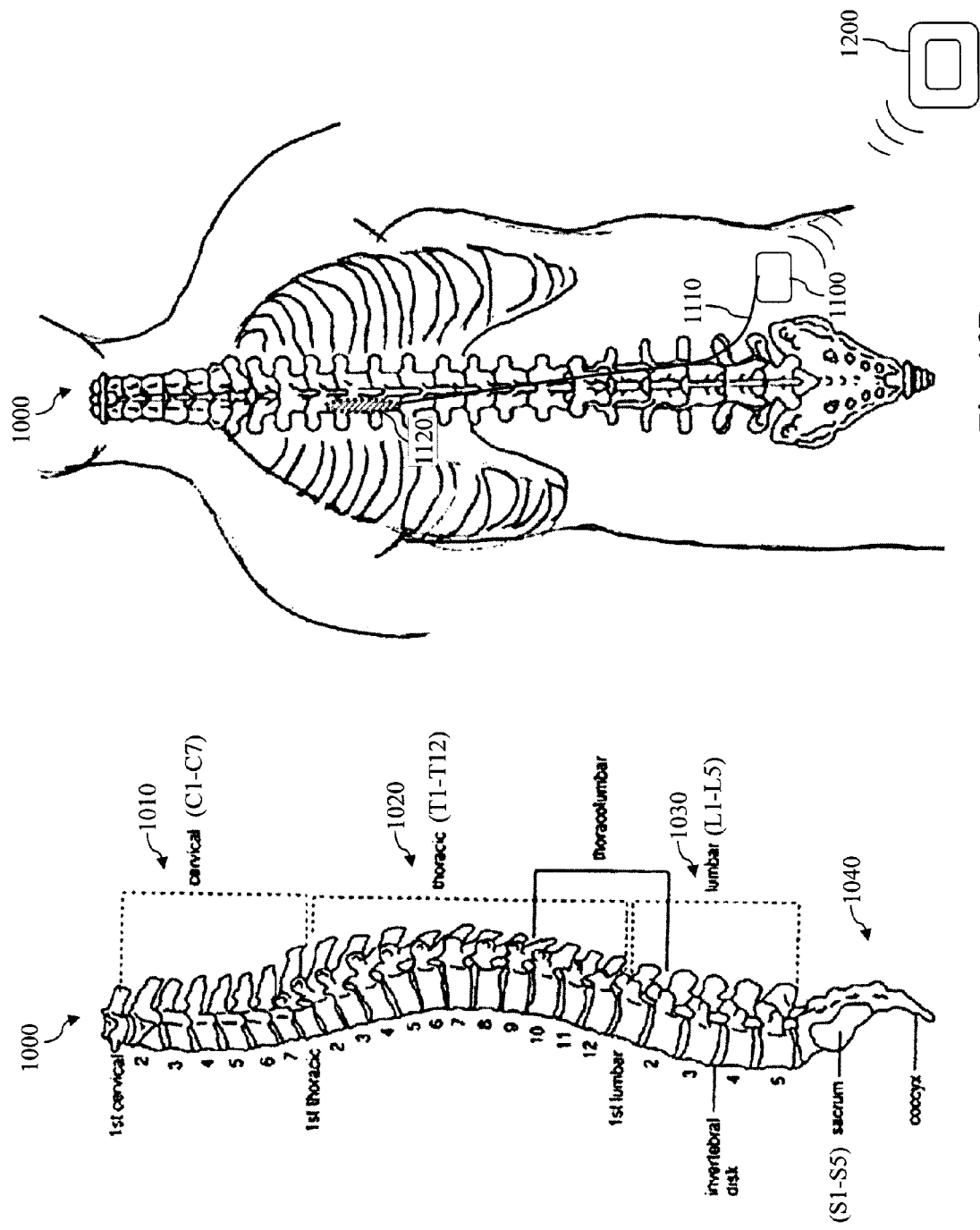

though electronic programming devices for controlling medical devices have been generally adequate for their intended purposes, they have not been entirely satisfactory in every aspect.

SYSTEM AND METHOD FOR USING CLINICIAN PROGRAMMER AND CLINICIAN PROGRAMMING DATA FOR INVENTORY AND MANUFACTURING PREDICTION AND CONTROL

BACKGROUND

As medical device technologies continue to evolve, active implantable medical devices have gained increasing popularity in the medical field. For example, one type of implantable medical device includes neurostimulator devices, which are battery-powered or battery-less devices that are designed to deliver electrical stimulation to a patient. Through proper electrical stimulation, the neurostimulator devices can provide pain relief for patients.

An implantable medical device (for example a neurostimulator) can be controlled using an electronic programming device such as a clinician programmer or a patient programmer. These programmers can be used by medical personnel or the patient to define the particular electrical stimulation therapy to be delivered to a target area of the patient's body, or alter one or more stimulation parameters of the electrical stimulation therapy. Advances in the medical device field have improved these electronic programmers. However, the capabilities of these electronic programmers have not been fully utilized. For example, the electronic programmers have not been fully utilized to facilitate the management of medical device inventory and/or manufacturing prediction and control.

Therefore, although electronic programming devices for controlling medical devices have been generally adequate for their intended purposes, they have not been entirely satisfactory in every aspect.

SUMMARY

One aspect of the present disclosure involves a medical system. The medical system includes: a medical device configured to deliver a medical therapy to a patient; a clinician programmer configured to program the medical device, wherein the clinician programmer includes: an integrated imaging device configured to acquire a visual representation of the medical device; a touch-sensitive graphical user interface configured to receive a medical device identifier of the medical device through manual user input; an electronic processor configured to generate an electronic ticket identifying the medical device based on the visual representation or the medical device identifier; and a communications device configured to send the electronic ticket to remote devices; and a manufacturing database defined on one or more computer servers configured to store and maintain an electronic inventory of a plurality of types of medical devices including the medical device for which the electronic ticket is generated, wherein the manufacturing database is configured to: receive the electronic ticket from the clinician programmer through communications conducted under a telecommunications protocol; and perform at least one of the following tasks in response to the received electronic ticket: updating the electronic inventory, analyzing a usage trend of the medical device, predicting a potential shortage of the medical device, and suggesting a production schedule for the medical device.

Another aspect of the present disclosure involves a portable electronic device for managing a medical device inventory. The portable electronic device includes: a transceiver component configured to conduct electronic communication with external devices; an imaging component configured to obtain a visual code associated with a medical device through a scan of the medical device; a touchscreen component configured to receive a medical device identifier associated with the medical device through manual input from a user; a memory storage component configured to store machine-readable code and the visual code or the medical device identifier of the medical device; and a computer processor component configured to execute the machine-readable code to perform the following tasks: identifying the medical device via the visual code obtained from the scan or the medical device identifier received through the manual input from the user; generating an electronic ticket for the medical device in response to the identifying of the medical device; and sending, via the transceiver, the electronic ticket to a database.

Yet another aspect of the present disclosure involves a method of using a portable electronic device to facilitate management of a medical device inventory. The method includes: identifying a medical device by performing at least one of the following actions: obtaining a visual code associated with the medical device via an imaging component of the portable electronic device; and obtaining a medical device identifier associated with the medical device via manual user input on a touchscreen display of the portable electronic device; generating an electronic ticket for the medical device in response to the identifying, wherein the electronic ticket contains at least one of the following: a make and model of the medical device, a serial number of the medical device, and a location of the medical device; sending the electronic ticket to a database; and receiving confirmation that the database has been updated based on the electronic ticket.

One more aspect of the present disclosure involves a method of managing a medical device inventory. The method includes: receiving, wirelessly from the clinician programmer, a registration report of a medical device, the registration report containing at least one of the following: an unique identifier of the medical device, an activation date of the medical device, and a location of the medical device; creating an electronic record for the medical device in a database in response to the received registration report; receiving, wirelessly from the clinician programmer, an electronic ticket associated with the medical device, wherein the electronic ticket contains usage information of the medical device; updating the electronic record in response to the received electronic ticket; and performing the following tasks based on the updating the electronic record: evaluating a usage trend of the medical device; forecasting a supply and demand of the medical device; and recommending a production schedule for the medical device.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIGS. 10A and 10B are side and posterior views of a human spine, respectively.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Electronic programmers have been used to configure or program active implantable medical devices such as neurostimulators so that they can be operated in a certain manner. These electronic programmers include clinician programmers and patient programmers, each of which may be a handheld device. A clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

Over the years, these electronic programmers have achieved significant improvements, for example, improvements in size, power consumption, lifetime, and ease of use. However, the capabilities of existing programmers have not been fully utilized. For example, medical devices such as neurostimulators are relatively expensive to manufacture and to maintain (e.g., due to sterilization expiration dates). Therefore, it is costly to maintain a high inventory of these medical devices. On the other hand, the inventory for the medical devices should not be kept too low either. One reason for not keeping a low inventory is that the manufacturing of these medical devices may be a lengthy process, but the need to have one of these medical devices deployed on a patient may arise suddenly (for example, if the patient needs a pacemaker). Another factor is that, even if the patient does not need the medical device urgently, an unnecessary delay for getting these medical devices may prolong the pain and suffering of a patient. Therefore, a manufacturer of these medical devices may wish to maintain a medical device inventory that is neither too high nor too low. Currently, clinician programmers have not been used to facilitate the inventory management or the manufacturing of the medical devices.

According to various aspects of the present disclosure, an infrastructure is implemented in which clinician programmers and their collected data are used to facilitate the inventory management and the manufacturing of medical devices. Various aspects of the electronic programmer and its corresponding infrastructure are now described in more detail below.

Figure 1:
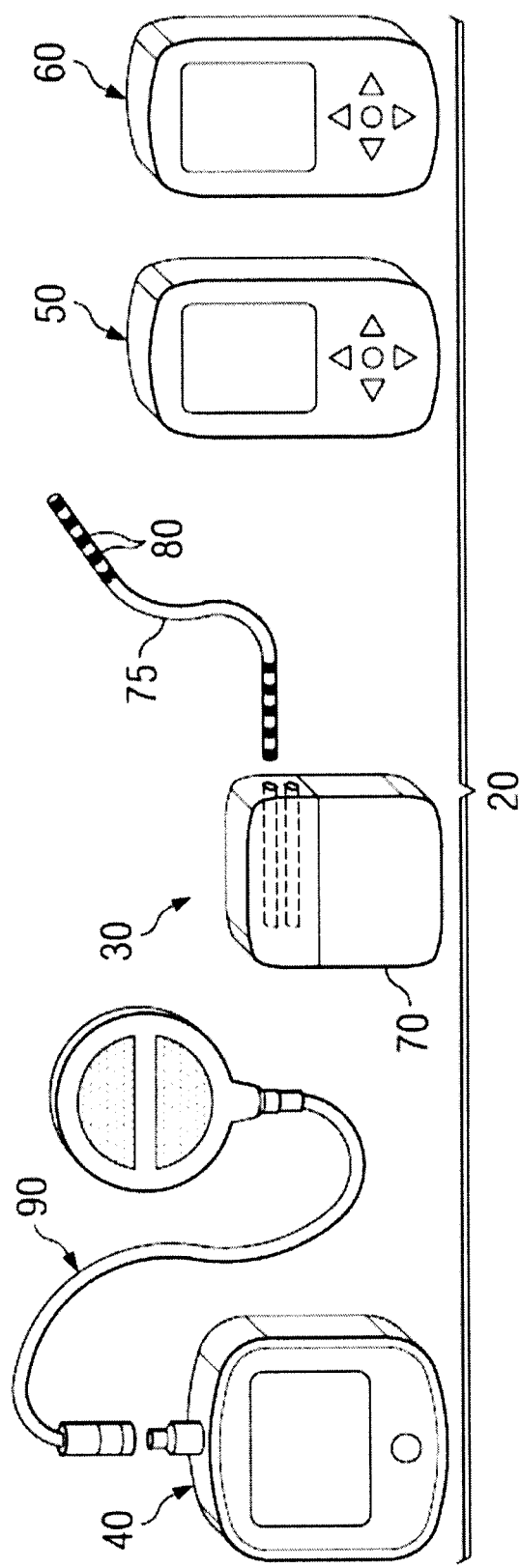
FIG. 1 is a simplified block diagram of a medical system according to various aspects of the present disclosure.

Referring to FIG. 1, a simplified block diagram of a medical device system 20 is illustrated to provide an example context of the various aspects of the present disclosure. The medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end of one or more percutaneous, or skin-penetrating, leads. The other end of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 60 is used as an example of the electronic programmer. However, it is understood that the electronic programmer may also be the patient programmer 50 or other touch screen programming devices (such as smart-phones or tablet computers) in other embodiments.

Figure 2:
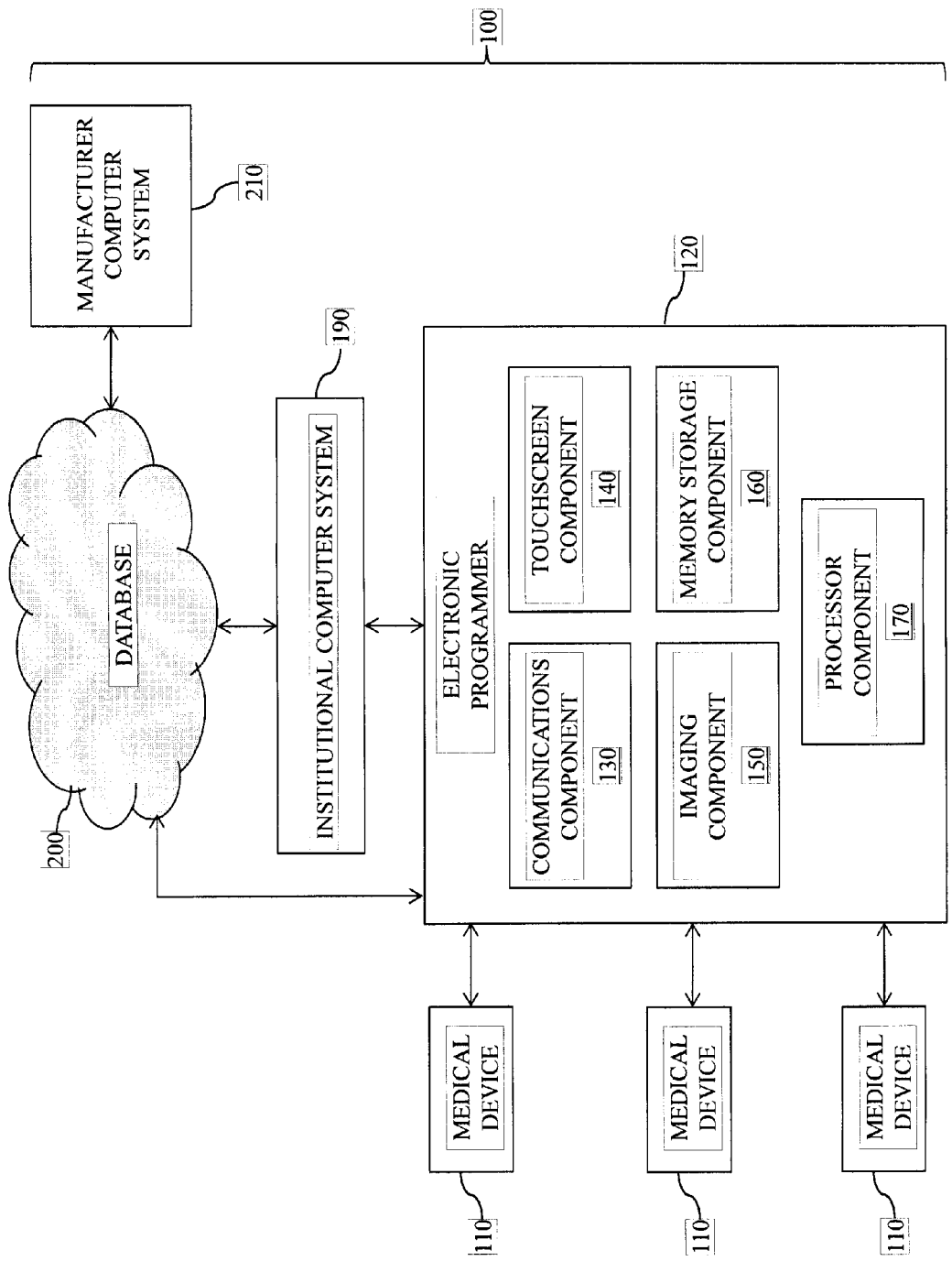
FIG. 2 is a simplified block diagram of a medical infrastructure according to various aspects of the present disclosure.

Referring now to FIG. 2, a simplified block diagram of a medical infrastructure 100 (which may also be considered a medical system) is illustrated according to various aspects of the present disclosure. The medical infrastructure 100 includes a plurality of medical devices 110. These medical devices 110 may each be a programmable medical device (or parts thereof) that can deliver a medical therapy to a patient. In some embodiments, the medical devices 110 may include a device of the neurostimulator system discussed above with reference to FIG. 1. For example, the medical devices 110 may be a pulse generator, an implantable lead, a charger, or portions thereof. It is understood that each of the medical devices 110 may be a different type of medical device. In other words, the medical devices 110 need not be the same type of medical device.

The medical infrastructure 100 also includes an electronic programmer 120. In some embodiments, the electronic programmer 120 may be a clinician programmer, for example the clinician programmer 60 of FIG. 1 (or a similar programmer). In other embodiments, the electronic programmer 120 may be a patient programmer, for example the patient programmer 50 of FIG. 1 (or a similar programmer). In further embodiments, it is understood that the electronic programmer may be a tablet computer. In any case, the electronic programmer 120 is configured to program the stimulation parameters of the medical devices 110 so that a desired medical therapy can be delivered to a patient.

The electronic programmer 120 contains a communications component 130 that is configured to conduct electronic communications with external devices. For example, the communications device 130 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (WiFi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 120 contains a touchscreen component 140. The touchscreen component 140 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 120 may optionally include additional user input/output components that work in conjunction with the touchscreen component 140 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 120 contains an imaging component 150. The imaging component 150 is configured to capture an image of a target device via a scan. For example, the imaging component 150 may be a camera in some embodiments. The camera may be integrated into the electronic programmer 120. The camera can be used to take a picture of a medical device, or scan a visual code of the medical device, for example its barcode or Quick Response (QR) code.

The electronic programmer contains a memory storage component 160. The memory storage component 160 may include system memory, (e.g., RAM), static storage 608 (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 160 (or a portion thereof) may be configured as a local database capable of storing electronic records of medical devices and/or their associated patients.

The electronic programmer contains a processor component 170. The processor component 170 may include a central processing unit (CPU), a graphics processing unit (GPU) a micro-controller, a digital signal processor (DSP), or another suitable electronic processor capable of handling and executing instructions. In various embodiments, the processor component 170 may be implemented using various digital circuit blocks (including logic gates such as AND, OR, NAND, NOR, XOR gates, etc.) along with certain software code. In some embodiments, the processor component 170 may execute one or more sequences computer instructions contained in the memory storage component 160 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 120 is not necessarily limited to the components 130-170 discussed above, but it may further include additional components that are used to carry out the programming tasks. These additional components are not discussed herein for reasons of simplicity. It is also understood that the medical infrastructure 100 may include a plurality of electronic programmers similar to the electronic programmer 120 discussed herein, but they are not illustrated in FIG. 2 for reasons of simplicity.

The medical infrastructure 100 also includes an institutional computer system 190. The institutional computer system 190 is coupled to the electronic programmer 120. In some embodiments, the institutional computer system 190 is a computer system of a healthcare institution, for example a hospital. The institutional computer system 190 may include one or more computer servers and/or client terminals that may each include the necessary computer hardware and software for conducting electronic communications and performing programmed tasks. In various embodiments, the institutional computer system 190 may include communications devices (e.g., transceivers), user input/output devices, memory storage devices, and computer processor devices that may share similar properties with the various components 130-170 of the electronic programmer 120 discussed above. For example, the institutional computer system 190 may include computer servers that are capable of electronically communicating with the electronic programmer 120 through the MICS protocol or another suitable networking protocol.

The medical infrastructure 100 includes a database 200. In various embodiments, the database 200 is a remote database—that is, located remotely to the institutional computer system 190 and/or the electronic programmer 120. The database 200 is electronically or communicatively (for example through the Internet) coupled to the institutional computer system 190 and/or the electronic programmer. In some embodiments, the database 200, the institutional computer system 190, and the electronic programmer 120 are parts of a cloud-based architecture. In that regard, the database 200 may include cloud-based resources such as mass storage computer servers with adequate memory resources to handle requests from a variety of clients. The institutional computer system 190 and the electronic programmer 120 (or their respective users) may both be considered clients of the database 200. In certain embodiments, the functionality between the cloud-based resources and its clients may be divided up in any appropriate manner. For example, the electronic programmer 120 may perform basic input/output interactions with a user, but a majority of the processing and caching may be performed by the cloud-based resources in the database 200. However, other divisions of responsibility are also possible in various embodiments.

The database 200 may be a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 200 is able to provide these functionalities at least in part via communication with the electronic programmer 120 and in response to the data sent by the electronic programmer 120. These functionalities of the database 200 and its communications with the electronic programmer 120 will be discussed in greater detail later.

The medical infrastructure 100 further includes a manufacturer computer system 210. The manufacturer computer system 210 is also electronically or communicatively (for example through the Internet) coupled to the database 200. Hence, the manufacturer computer system 210 may also be considered a part of the cloud architecture. The computer system 210 is a computer system of medical device manufacturer, for example a manufacturer of the medical devices 110 and/or the electronic programmer 120.

In various embodiments, the manufacturer computer system 210 may include one or more computer servers and/or client terminals that each includes the necessary computer hardware and software for conducting electronic communications and performing programmed tasks. In various embodiments, the manufacturer computer system 210 may include communications devices (e.g., transceivers), user input/output devices, memory storage devices, and computer processor devices that may share similar properties with the various components 130-170 of the electronic programmer 120 discussed above. Since both the manufacturer computer system 210 and the electronic programmer 120 are coupled to the database 200, the manufacturer computer system 210 and the electronic programmer 120 can conduct electronic communication with each other.

The medical infrastructure 100 can be used to provide quick and reliable tracking of medical devices (including the electronic programmers) and facilitate inventory management for these medical devices. This is explained in FIGS. 3-8 and the corresponding discussions below.

Figure 3:
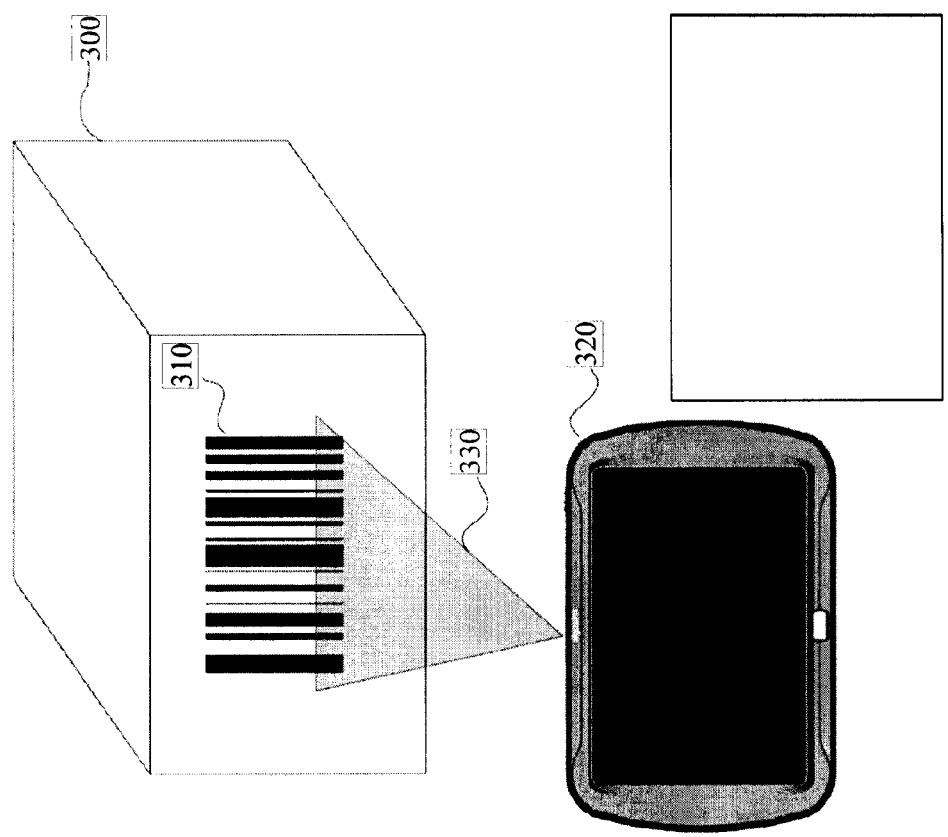
FIGS. 3-8 are flowcharts of different methods for implementing a medical device inventory management according to various aspects of the present disclosure.

FIG. 3 is a simplified block diagram illustrating how an electronic programmer such as a clinician programmer can be used to obtain identification information of a desired medical device. For example, a desired medical device such as an IPG (or other parts of a neurostimulator system) may be located inside a box 300. A visual code 310 associated with the medical device may be displayed on the box 300 (or may be embedded in the medical device itself). In some embodiments, the visual code 310 may include a barcode or a Quick Response (QR) code. In other embodiments, the visual code 310 may include other types of unique identification information associated with the medical device, such as the make and model, product number, or serial number of the medical device.

An electronic device 320 with imaging capabilities may be used to scan the visual code 310 by way of a radiation beam 330. In some embodiments, the electronic device 320 may be a clinician programmer, for example as an embodiment of the electronic programmer 120 of FIG. 2. The clinician programmer includes an integrated camera, for example as an embodiment of the imaging component 150 of FIG. 2. The integrated camera can be used to output the radiation beam 330 or to perform the imaging of the medical device inside the box 310. In some embodiments, the integrated camera scans the visual code 310. In other embodiments, the integrated camera takes a picture of the medical device inside the box 300. A more detailed discussion of selecting a virtual reality representation of the desired medical device via scanning is found in U.S. patent application Ser. No. 13/601,449, entitled "Virtual Reality Representation Of Medical Devices," and filed on Aug. 31, 2012, the content of which is incorporated herein by reference in its entirety.

As the visual code 310 (or a picture of the medical device) associated with the medical device is scanned into the electronic device 320, the electronic device 320 may search an electronic database for matching information so as to identify the device. The database may be a local database to the electronic device 320 or may be a remote cloud-based database such as the database 200 of FIG. 2.

Figure 4:
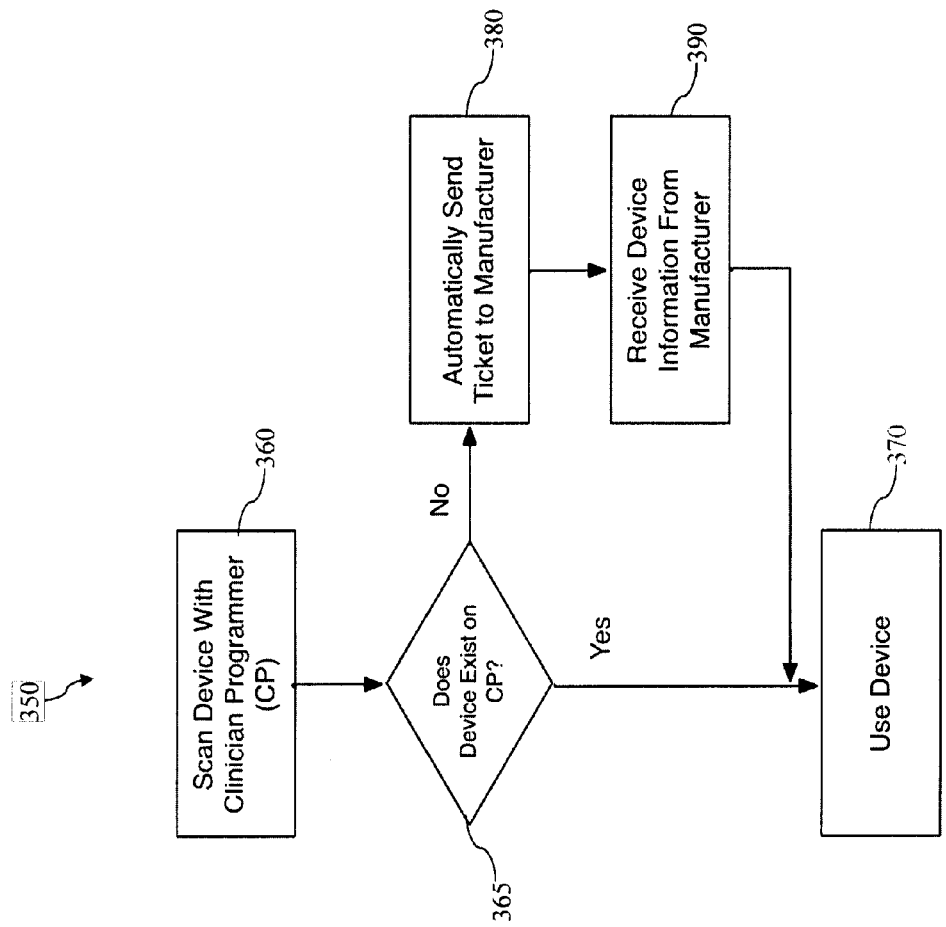

Referring to FIG. 4, a simplified flowchart of a method 350 is illustrated that describes a user experience with the tracking process for clinician programmers and other medical devices.

The method 350 includes a step 360, in which a medical device is scanned with the clinician programmer. Alternatively, the user may also have the option of inputting the medical device identification information manually in the clinician programmer, for example typing the medical device identification information through a touch-sensitive graphical user interface of the clinician programmer. The method 350 then proceeds to a decision step 365 to determine whether the medical device (that is scanned) exists on the clinician programmer. In other words, the decision step 365 determines whether the medical device is recognized by the clinician programmer. If the answer is yes, then the method 350 proceeds to step 370 to use the device. If the answer is no, the method 350 proceeds to step 380, in which a ticket is automatically sent to a manufacturer. From this point forward, the use of the clinician programmer can be tracked by the mere use of the clinician programmer, for example whenever the user (for example, a healthcare professional) uses the clinician programmer to program a neurostimulator. Thereafter, the method 350 proceeds to step 390, in which device information from the manufacturer is received. Thereafter, the method 350 proceeds to step 370 to use the device again.

Figure 5:
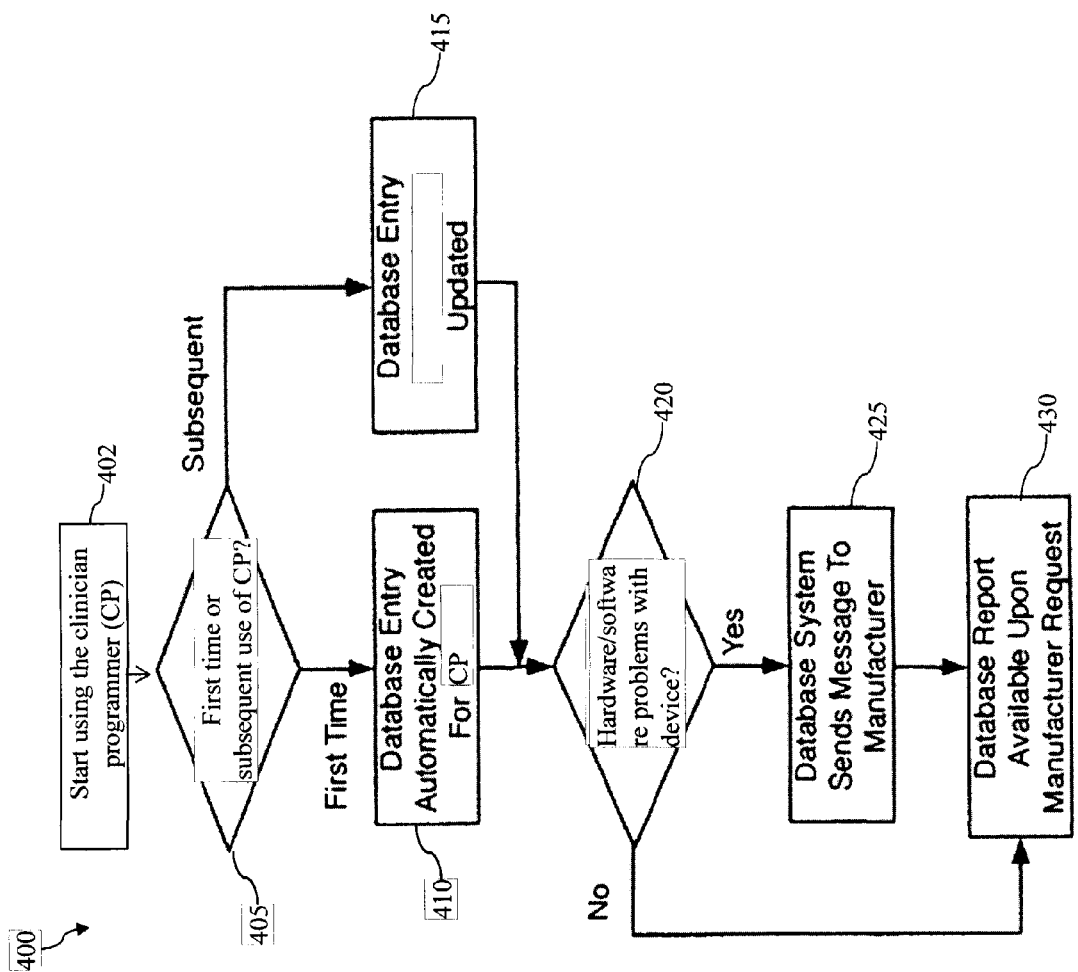

FIG. 5 is a simplified method 400 illustrating a medical device tracking process according to various aspects of the present disclosure. The method 400 begins with a step 402 to start using the clinician programmer (CP). The method 400 proceeds to a decision step 405 to determine whether the CP is used for the first time. The device may be the medical device scanned by the clinician programmer, or may be the clinician programmer itself. If the device is used for the first time, the method 400 proceeds to step 410 to automatically create a database entry for the CP. The database entry may be created on a remote database such as the database 200 of FIG. 2, for example. The creation of the database entry may be done through sending a registration report (or a registration ticket) to the database. The registration report may include information such as the serial number of the device, the activation date of the device, and the location (e.g., hospital/country/region) of the activation.

If the device is not used for the first time, the method 400 proceeds to step 415 to update the previously created database entry. The updating of the data entry may be done through an electronic ticket sent to the database from the clinician programmer. The electronic ticket may be generated in response to the scanning of the visual code or of an image of the device as discussed above with reference to FIGS. 3-4.

In step 420, any discovered hardware or software problem of the CP is reported to the database. This may be done via the registration report generated in step 410 or the electronic ticket generated in step 415. If there are hardware or software problems, the database system 425 may send a corresponding message to the manufacturer, letting the manufacturer know that there are problems with the device. Thereafter, the database can provide a report upon the manufacturer's request in step 430. Such report to the manufacturer can include forecast information, usage of the medical device, regional differences, etc. If no hardware or software problems exist, the database can still provide the report in step 430. This whole process provides to the manufacturer about actual usage trends of the device, for example, whether the device is malfunctioning or broken and needs replacement soon. The manufacturer may therefore make more accurate projections/forecasts involving their products.

Figure 6:
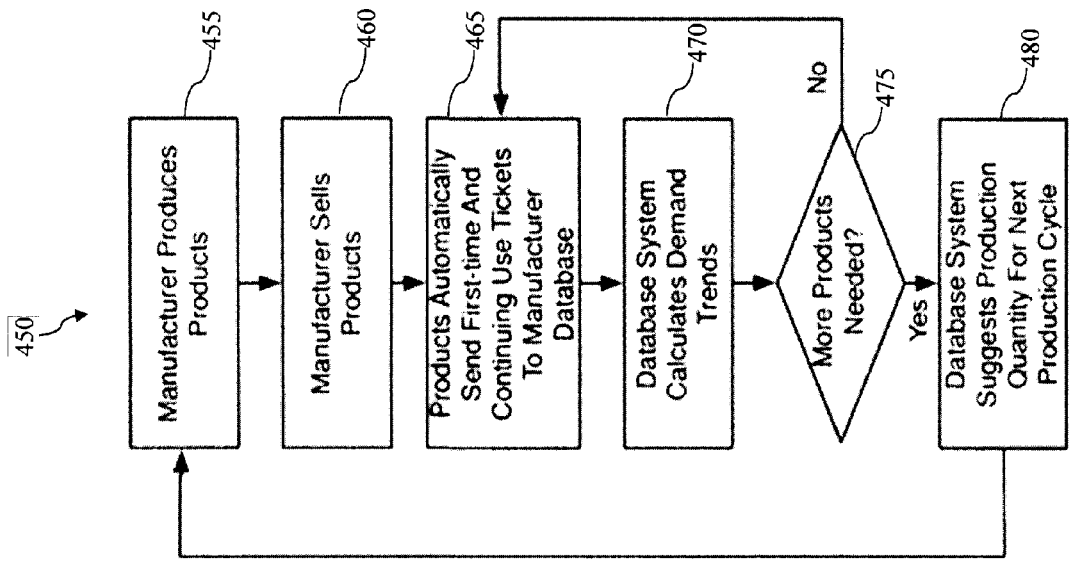

FIG. 6 is a simplified method 450 illustrating an inventory and manufacturing control according to various aspects of the present disclosure. The method 450 includes a step 455, in which the manufacturer of one or more medical devices produces products (i.e., implantable medical devices and/or programmers). The method 450 proceeds to step 460, in which the manufacturer sells the products.

Thereafter, in step 465, the products (while being used in the field) automatically send first-time registration reports and continuing use tickets to the manufacturer's database. For example, a registration report of the product (be it a clinician programmer or an implantable medical device) upon its first use, which is sent to the database to create an electronic entry of the product in the database. Upon the product's subsequent use, an electronic ticket can be generated, which is sent to the database to update the entry of the product. In various embodiments, the electronic ticket may contain information such as a make and model of the product, a serial number (either a printed label on the packaging or an embedded within) of the product, a location of the product, a usage trend analysis of the product, and distribution points of the product, etc. In some embodiments, the electronic ticket may include information for multiple products of the manufacturer. Also, the electronic ticket may be devoid of patient information in some embodiments, so as to protect the patient's privacy.

Based on the entries for these products, the database system calculates the demand and usage trends of the product in step 470. The method 450 then proceeds to a decision step 475 to determine whether more products are needed based on the demand and usage trends calculated in step 470. If the answer is yes, the method 450 proceeds to step 480, in which the database system suggests production quantity for the next production cycle. If the answer from the decision step 475 is no, the method 450 loops back to step 465.

Figure 7:
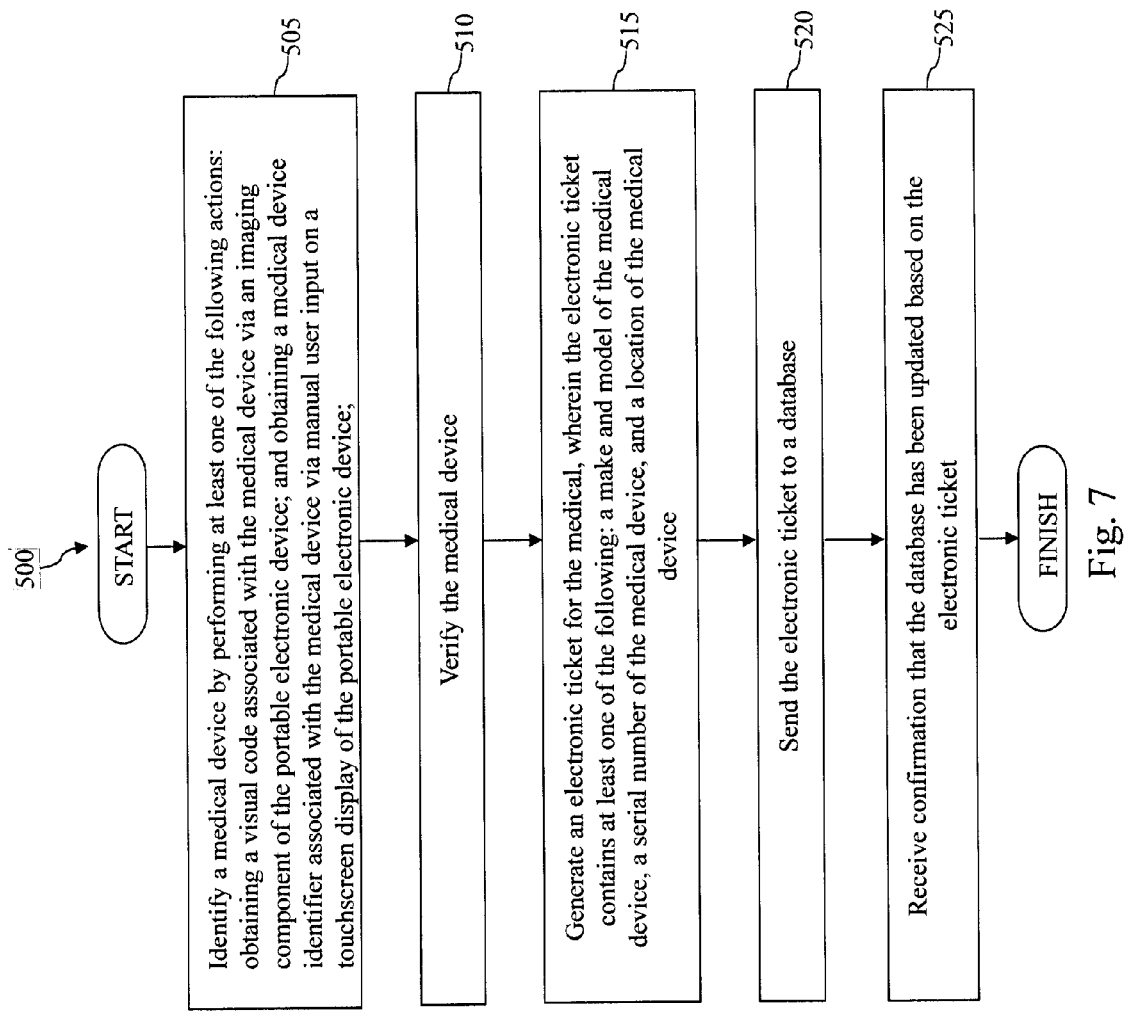

FIG. 7 is a simplified flowchart of a method 500 of using a portable electronic device to facilitate management of a medical device inventory according to various aspects of the present disclosure. In some embodiments, the portable electronic device includes a clinician programmer configured to program various stimulation parameters of the medical device (e.g., a neurostimulator) to deliver a stimulation therapy for a patient. Therefore, the steps of the method 500 are performed from the perspective of the portable electronic device such as the clinician programmer.

The method 500 includes a step 505, in which a medical device is identified. The identification of the medical device may be done by obtaining a visual code associated with the medical device via an imaging component of the portable electronic device. The visual code associated with the medical device may include at least one of: a barcode and a Quick Response (QR) code. In some embodiments, the imaging component includes an integrated camera configured to scan the visual code of the medical device. The identification of the medical device may also be done by obtaining a medical device identifier associated with the medical device via a manual user input on a touchscreen display of the portable electronic device. The medical device identifier associated with the medical device may include at least one of: a serial number of the medical device and a product number of the medical device. In certain embodiments, the touchscreen display is configured to display a touch-sensitive virtual keyboard through which the manual user input is received.

The method 500 includes a step 510, in which the medical device is verified. In some embodiments, the verification of the medical device includes prompting the user to confirm that the electronic ticket correctly represents the medical device. The user may be presented with a visual representation of the detected medical device, so he can confirm that it is indeed the right medical device. This verification step helps ensure that the information for the correct medical device is sent to the database. In other embodiments, the verification of the medical device includes communicating with a database to confirm that the medical device is an authentic device from a specific manufacturer, and thereafter providing an indication (for example through a message displayed on the clinician programmer) to the user as to the authenticity of the medical device based on the communicating. In this manner, the user may be alerted when the medical device is a counterfeit device and may take appropriate actions accordingly.

The method 500 includes a step 515, in which an electronic ticket is generated for the medical device in response to the identification step 505 and/or the verification step 510. The electronic ticket contains at least one of the following: a make and model of the medical device, a serial number of the medical device, and a location of the medical device. The electronic ticket may also include a usage trend analysis or distribution points of the medical device. In some embodiments, the electronic ticket may include information for multiple medical devices.

The method 500 includes a step 520, in which the electronic ticket is sent to a database. In some embodiments, the database is a remote database communicatively coupled to the portable electronic device. In other embodiments, the database is a local database implemented on the portable electronic device. In that case, the local database may be synced with the remote database periodically.

The method 500 includes a step 525, in which confirmation is received by the portable electronic device that the database has been updated based on the electronic ticket. The communication between the portable electronic device and the remote database may be performed by a transceiver of the portable electronic under a suitable wireless telecommunications protocol.

It is understood that the steps 505-525 of the method 500 described herein are merely example steps according to some embodiments. These steps may be omitted or modified in certain embodiments. In various other embodiments, the method 500 may also include additional steps performed before, during, or after the steps 505-525. As an example, the method 500 may include a step to generate and send a registration report of the clinician programmer upon its first use. The registration report may contain at least one of the following: a serial number of the clinician programmer, an activation date of the clinician programmer, and a location of the clinician programmer.

Figure 8:
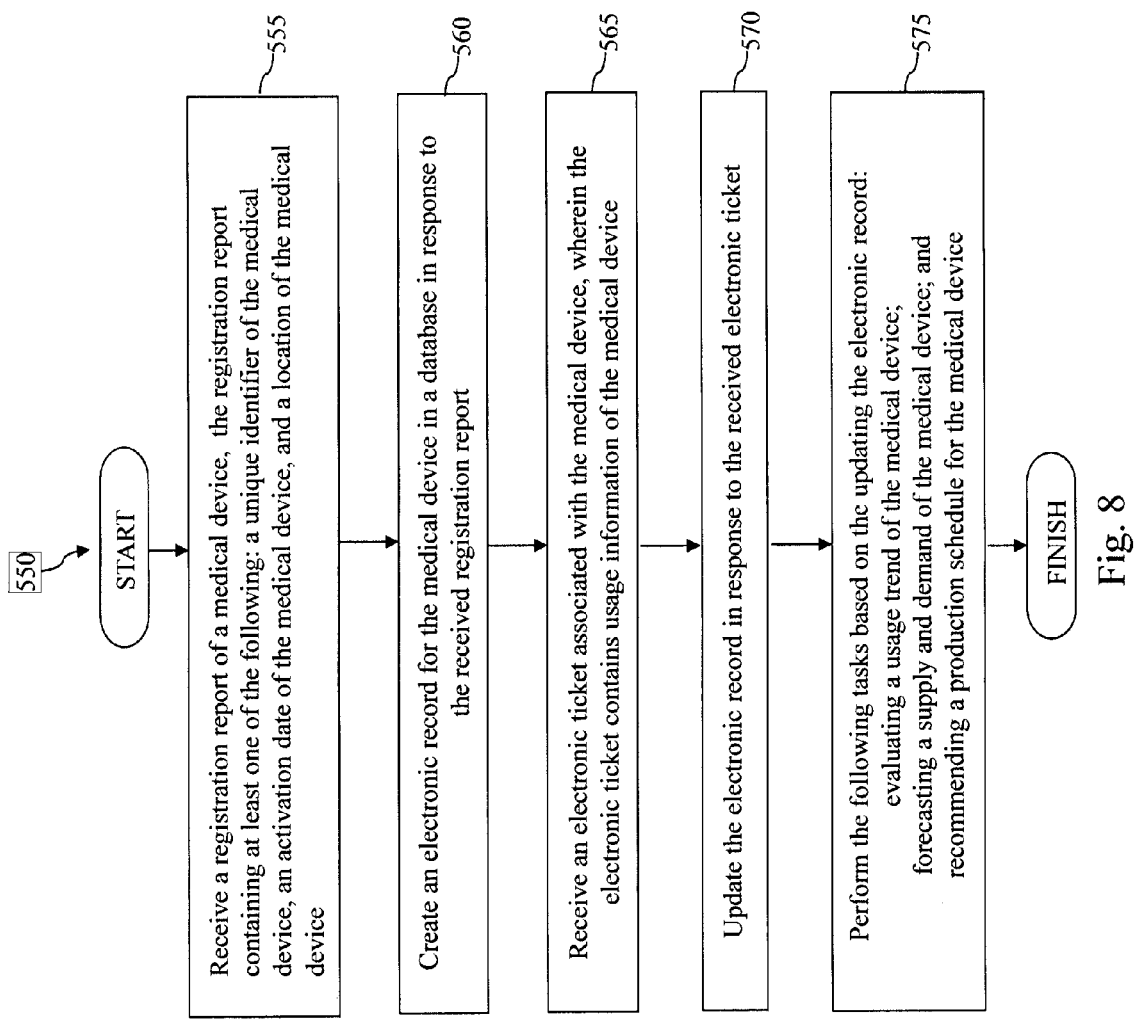

FIG. 8 is a simplified flowchart of a method 550 of managing a medical device inventory according to various aspects of the present disclosure. Whereas the steps of the method 500 of FIG. 7 are performed from the perspective of the portable electronic device (such as the clinician programmer), the steps of the method 550 are performed from the perspective of a remote database (for example a manufacturer database) communicatively coupled to the portable electronic device.

In some embodiments, the medical device whose inventory is to be managed may be a programmable medical device capable of delivering a stimulation therapy to a patient. For example, the medical device may be a part of a neurostimulator. In other embodiments, the medical device may be the clinician programmer capable of programming the programmable medical device.

The method 550 includes a step 555, in which a registration report of a medical device is received. The registration report may be received wirelessly from a clinician programmer. The registration report may contain at least one of the following: a unique identifier of the medical device (for example the product and serial number), an activation date of the medical device, and a location of the medical device.

The method 550 includes a step 560, in which an electronic record is created for the medical device in a database in response to the received registration report.

The method 550 includes a step 565, in which an electronic ticket associated with the medical device is received. The electronic ticket may also be received wirelessly from the clinician programmer. In some embodiments, the electronic ticket contains usage information of the medical device. In some embodiments, the electronic ticket is generated by the clinician programmer at least in part in response to imaging the medical device via a camera integrated on the clinician programmer. In other embodiments, the electronic ticket is generated by the clinician programmer at least in part in response to receiving a manual user via a touch-sensitive user interface of the clinician programmer.

The method 550 includes a step 570, in which the electronic record is updated in response to the received electronic ticket.

The method 550 includes a step 575, in which the following tasks are performed based on the updating the electronic record: evaluating a usage trend of the medical device; forecasting a supply and demand of the medical device; and recommending a production schedule for the medical device.

It is understood that the steps 555-575 of the method 550 described herein are merely example steps according to some embodiments. These steps may be omitted or modified in certain embodiments. In certain other embodiments, the method 550 may also include additional steps performed before, during, or after the steps 555-575. As an example, the method 550 may include a step to sync the database with a local database on the clinician programmer. As another example, the method 550 may include a step to send confirmation to the clinician programmer that the registration report and the electronic ticket have been received.

The system and method of managing an electronic medical device inventory discussed above offers various advantages. It is understood, however, that not all advantages are discussed herein, different embodiments may offer different advantages, and no embodiment is limited to particular advantages.

One advantage of the present disclosure pertains to knowledge of current medical devices. Previously, a manufacturer database may not have update-to-date knowledge of the medical devices currently deployed in the field. In comparison, the clinician programmer is able to acquire the information of currently deployed (or about to be deployed) medical devices (for example by an imaging scan) and then relay that information electronically to the manufacturer's database in the form of electronic tickets. Whenever the clinician programmer is in communication with a target medical device—which may occur during programming of the medical device, for example—a new electronic ticket can be generated and sent to the manufacturer's database to update its electronic inventory of medical devices. In this manner, the manufacturer's database of the present disclosure is able to have accurate and substantially real-time knowledge of medical devices in its inventory.

Based on such accurate and up-to-date knowledge, the manufacturer's database can perform management related tasks such as analyzing usage trends, forecasting equipment shortages, projecting shipping delays, suggesting production schedules, etc. By doing so, the actual inventory of the medical devices can be maintained to be at an optimum level, neither too high (which would be costly) nor too low (which may lead to delays). In other words, the manufacturer's database, through its communications with the clinician programmers in the field, is able to automatically manage its medical device inventory to prevent an overt-stocking or an understocking situation.

Another advantage of the present disclosure is that the communications between the manufacturer's database and the clinician programmers take place electronically and automatically, requiring minimal user involvement. This simplifies the duties of the user of the clinician programmer. For example, a sales representative operating the clinician programmer need not manually request and send usage data for the medical devices, thereby eliminating potential errors that could otherwise occur. Furthermore, the tracking and maintenance of the inventory is now done online instead of through manual logs. This allows not only the manufacturer, but also its clients, quick and convenient access to the database to extract information that it needs.

Through the discussions above use an implantable neurostimulator as an example of the medical that can be tracked, it is understood that the various aspects of the present disclosure are applicable to any type of medical devices.

Figure 9:
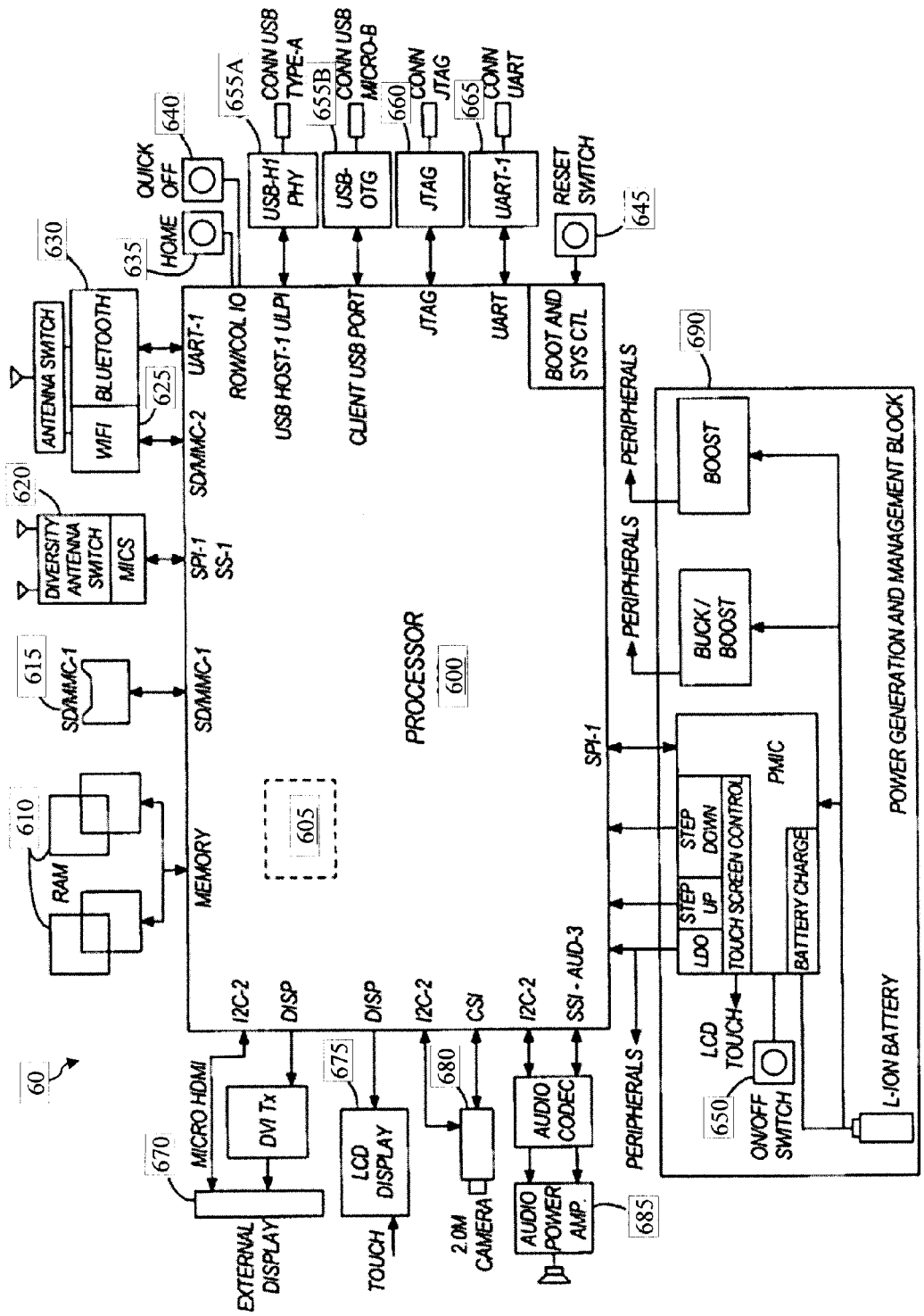
FIG. 9 is a simplified block diagram of an electronic programmer according to various aspects of the present disclosure.

FIG. 9 shows a block diagram of one embodiment of the clinician programmer (CP) 60 (FIG. 1) that can be used to display the visual representations of a medical therapy discussed above. It is understood, however, that alternative embodiments of the CP may be used to perform these representations as well.

The CP includes a printed circuit board ("PCB") that is populated with a plurality of electrical and electronic components that provide power, operational control, and protection to the CP. With reference to FIG. 9, the CP includes a processor 600. The processor 600 controls the CP. In one construction, the processor 600 is an applications processor model i.MX515 available from Freescale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX51CEC, Rev. 4" data sheet dated August 2010 and published by Freescale Semiconductor® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 9 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 9.

The CP includes multiple bi-directional radio communication capabilities. Specific wireless portions included with the CP are a Medical Implant Communication Service (MICS) bi-directional radio communication portion 620, a WiFi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The WiFi portion 625 and Bluetooth portion 630 include a WiFi communication interface, a Bluetooth communication interface, an antenna switch, and a related antenna all of which allows wireless communication following the WiFi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 9.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 9) may also be included for data transfer.

It is understood that a patient programmer may be implemented in a similar manner as the clinician programmer shown in FIG. 9. Furthermore, though the various visual representation concepts of the present disclosure are explained using an implanted pulse generator (IPG) as an example, it is understood that these concepts may apply to other types of implantable medical devices as well, such as pacemakers, etc.

FIG. 10A is a side view of a spine 1000, and FIG. 10B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 10B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 9.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A medical system, comprising:
a medical device configured to deliver a medical therapy to a patient;
a clinician programmer configured to program the medical device, wherein the clinician programmer includes:
an integrated imaging device configured to acquire a visual representation of the medical device;
a touch-sensitive graphical user interface configured to receive a medical device identifier of the medical device through manual user input;
a memory storage configured to store patient information;
an electronic processor configured to generate an electronic ticket identifying the medical device based on the visual representation or the medical device identifier, wherein the electronic ticket is generated to be devoid of patient privacy information; and
a communications device configured to send the electronic ticket to remote devices; and
a manufacturing database defined on one or more computer servers configured to store and maintain an electronic inventory of a plurality of types of medical devices including the medical device for which the electronic ticket is generated, wherein the manufacturing database is configured to:
receive the electronic ticket from the clinician programmer through communications conducted under a telecommunications protocol; and
perform at least one of the following tasks in response to the received electronic ticket: updating the electronic inventory, analyzing a usage trend of the medical device, predicting a potential shortage of the medical device, and suggesting a production schedule for the medical device.

2. The medical system of claim 1, wherein the clinician programmer is configured to prompt the user, via the touch-sensitive graphical user interface, to confirm that the electronic ticket correctly represents the medical device.

3. The medical system of claim 1, wherein the manufacturing database is configured to communicate with the clinician programmer to:
verify an authenticity of the medical device; and
provide an indication of the authenticity of the medical device to a user through the clinician programmer.

4. The medical system of claim 1, wherein the electronic ticket contains at least one of the following information: a make and model of the medical device, a serial number of the medical device, and a location of the medical device, a usage analysis of the medical device, and a demand forecast of the medical device.

5. The medical system of claim 1, wherein the visual representation of the medical device includes at least one of: a barcode of the medical device, a Quick Response (QR) code of the medical device, and a picture of the medical device.

6. The medical system of claim 1, wherein the medical device identifier of the medical device includes at least one of: a serial number of the medical device and a product number of the medical device.

7. The medical system of claim 1, wherein:
the imaging device includes a digital camera; and
the touch-sensitive graphical user interface includes a touchscreen display responsive to gesture-based user interactions.

8. The medical system of claim 1, wherein the telecommunications protocol is a wireless protocol.

9. The medical system of claim 1, wherein the medical device includes one or more components of a neurostimulator system.

10. The medical system of claim 9, wherein the medical device includes a pulse generator or an electrode-containing lead.

11. The medical system of claim 1, wherein the electronic ticket is capable of identifying multiple medical devices.

12. The medical system of claim 1, wherein the electronic ticket is generated in response to a programming of the medical device by the clinician programmer.

13. A portable electronic device for managing a medical device inventory, the portable electronic device comprising:
a transceiver component configured to conduct electronic communication with external devices;
an imaging component configured to obtain a visual code associated with a medical device through a scan of the medical device;
a touchscreen component configured to receive a medical device identifier associated with the medical device through manual input from a user;
a memory storage component configured to store machine-readable code and the visual code or the medical device identifier of the medical device, and wherein the memory storage component is further configured to store patient information; and
a computer processor component configured to execute the machine-readable code to perform the following tasks:
identifying the medical device via the visual code obtained from the scan or the medical device identifier received through the manual input from the user;
generating an electronic ticket for the medical device in response to the identifying of the medical device, wherein the electronic ticket is devoid of patient privacy information but contains one or more of the following: a make and model of the medical device, a serial number of the medical device, a location of the medical device, and a demand forecast of the medical device; and
sending, via the transceiver, the electronic ticket to a database.

14. The portable electronic device of claim 13, wherein the computer processor component is configured to execute the machine-readable code to further perform: prompting the user to verify the medical device after the identifying and before the generating the electronic ticket.

15. The portable electronic device of claim 13, wherein the portable electronic device is a clinician programmer configured to program the medical device to deliver a medical therapy to a patient.

16. The portable electronic device of claim 15, wherein the generating the electronic ticket is performed during a programming session of the medical device.

17. The portable electronic device of claim 15, wherein the computer processor component is configured to execute the machine-readable code to further perform: generating and sending a registration report of the clinician programmer or the medical device upon an initial use.

18. The portable electronic device of claim 15, wherein the registration report contains at least one of the following: a serial number, an activation date, and a location of the clinician programmer or the medical device.

19. The portable electronic device of claim 13, wherein the imaging component includes an integrated digital camera, and wherein the touchscreen component is configured to display visual information captured by the digital camera.

20. The portable electronic device of claim 13, wherein the visual code associated with the medical device includes at least one of: a barcode and a Quick Response (QR) code.

21. The portable electronic device of claim 13, wherein the medical device identifier associated with the medical device includes at least one of: a serial number of the medical device and a product number of the medical device.

22. The portable electronic device of claim 13, wherein the medical device includes a neurostimulator.

23. The portable electronic device of claim 13, wherein the transceiver component, the imaging component, the touch screen component, the memory storage component, and the computer processor component are integrated into a single package.

24. A method of using a portable electronic device to facilitate management of a medical device inventory, the method comprising:
identifying a medical device by performing at least one of the following actions:
obtaining a visual code associated with the medical device via an imaging component of the portable electronic device; and
obtaining a medical device identifier associated with the medical device via manual user input on a touchscreen display of the portable electronic device;
programming the medical device via the portable electronic device;
generating an electronic ticket for the medical device in response to the identifying, wherein the electronic ticket is devoid of patient privacy information but contains at least one of the following: a make and model of the medical device, a serial number of the medical device, and a location of the medical device;
sending the electronic ticket to a database; and
receiving confirmation that the database has been updated based on the electronic ticket.

25. The method of claim 24, wherein the portable electronic device includes a clinician programmer configured to program various stimulation parameters of the medical device to deliver a stimulation therapy for a patient.

26. The method of claim 25, further comprising, before the identifying the medical device: generating and sending a registration report of the clinician programmer upon its first use, wherein the registration report contains at least one of the following: a serial number of the clinician programmer, an activation date of the clinician programmer, and a location of the clinician programmer.

27. The method of claim 24, further comprising: verifying the medical device after the identifying the medical device and before the generating the electronic ticket.

28. The method of claim 27, wherein the verifying comprises prompting the user to confirm that the electronic ticket correctly represents the medical device.

29. The method of claim 27, wherein the verifying comprises:
communicating with a database to confirm that the medical device is an authentic device from a specific manufacturer; and
providing an indication to the user based on the communicating.

30. The method of claim 24, wherein:
the imaging component includes an integrated camera configured to scan the medical device; and
the touchscreen display is configured to display a touch-sensitive virtual keyboard through which the manual user input is received.

31. The method of claim 24, wherein:
the visual code associated with the medical device includes at least one of: a barcode and a Quick Response (QR) code; and
the medical device identifier associated with the medical device includes at least one of: a serial number of the medical device and a product number of the medical device.

32. The method of claim 24, wherein the database is a local database, and further comprising: syncing the local database with a remote database.

33. The method of claim 24, wherein the database is a remote database, and wherein the sending the electronic ticket and the receiving the confirmation are each performed by a transceiver of the portable electronic under a wireless telecommunications protocol.

34. The method of claim 24, wherein the generating of the electronic ticket is performed in response to the programming of the medical device.

35. A method of managing a medical device inventory, the method comprising:
receiving, wirelessly from a clinician programmer during an initial programming session of a medical device, a registration report of the medical device, the registration report containing at least one of the following: a unique identifier of the medical device, an activation date of the medical device, and a location of the medical device;
creating an electronic record for the medical device in a database in response to the received registration report;
receiving, wirelessly from the clinician programmer during a subsequent programming session of the medical device, an electronic ticket associated with the medical device, wherein the electronic ticket contains usage information of the medical device;
updating the electronic record in response to the received electronic ticket; and
performing the following tasks based on the updating the electronic record:
evaluating a usage trend of the medical device;
forecasting a supply and demand of the medical device; and
recommending a production schedule for the medical device.

36. The method of claim 35, wherein the electronic ticket is generated by the clinician programmer at least in part in response to imaging the medical device via a camera integrated on the clinician programmer.

37. The method of claim 35, wherein the electronic ticket is generated by the clinician programmer at least in part in response to receiving a manual user via a touch-sensitive user interface of the clinician programmer.

38. The method of claim 35, further comprising: syncing the database with a local database on the clinician programmer.

39. The method of claim 35, wherein the medical device includes one or more parts of a neurostimulator system that is configurable by the clinician programmer to deliver a stimulation therapy to a patient.

40. The method of claim 35, further comprising: sending confirmation to the clinician programmer that the registration report and the electronic ticket have been received.

41. The method of claim 35, wherein the registration report is received before the electronic ticket is received.

* * * * *